US00PP26382P2

(12) United States Plant Patent
Tas

(10) Patent No.: US PP26,382 P2
(45) Date of Patent: Feb. 2, 2016

(54) ***ALSTROEMERIA* PLANT NAMED 'TESHUNTE'**

(50) Latin Name: *Alstroemeria hybrida*
Varietal Denomination: Teshunte

(71) Applicant: Marius Tas, De Kwakel (NL)

(72) Inventor: Marius Tas, De Kwakel (NL)

(73) Assignee: VOF Hortipartners, Heerhugowaard (NL)

( * ) Notice: Subject to any disclaimer, the term of this patent is extended or adjusted under 35 U.S.C. 154(b) by 95 days.

(21) Appl. No.: 13/999,717

(22) Filed: Mar. 17, 2014

(51) Int. Cl.
*A01H 5/02* (2006.01)

(52) U.S. Cl.
USPC ..... Plt./309

(58) Field of Classification Search
USPC ..... Plt./309
See application file for complete search history.

*Primary Examiner* — Susan McCormick Ewoldt
(74) *Attorney, Agent, or Firm* — C. A. Whealy

(57) ABSTRACT

A new and distinct cultivar of *Alstroemeria* plant named 'Teshunte', characterized by its broadly upright plant habit; medium to long flowering stems; sturdy and strong plants; moderately vigorous growth habit; numerous red orange and yellow-colored flowers; and good garden performance.

1 Drawing Sheet

Botanical designation: *Alstroemeria hybrida.*
Cultivar denomination: 'TESHUNTE'.

BACKGROUND OF THE INVENTION

The present invention relates to a new and distinct cultivar of *Alstroemeria* plant, botanically known as *Alstroemeria hybrida*, grown typically as a potted garden *Alstroemeria*, and hereinafter referred to by the name 'Teshunte'.

The new *Alstroemeria* plant is a product of a planned breeding program conducted by the Inventor in Heerhugowaard, The Netherlands. The objective of the breeding program is to create new potted garden *Alstroemeria* plants that flower continuously and with numerous attractive flowers.

The new *Alstroemeria* plant is a naturally-occurring branch mutation of *Alstroemeria hybrida* 'Tesronto', not patented. The new *Alstroemeria* plant was discovered and selected by the Inventor on a single flowering plant from within a population of plants of 'Tesronto' in a controlled greenhouse environment in Heerhugowaard, The Netherlands in June, 2010.

Asexual reproduction of the new *Alstroemeria* plant by root divisions in a controlled greenhouse environment in Heerhugowaard, The Netherlands since September, 2010 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Teshunte'. These characteristics in combination distinguish 'Teshunte' as a new and distinct *Alstroemeria* plant:

1. Broadly upright plant habit; medium to long flowering stems.
2. Sturdy and strong plants; moderately vigorous growth habit.
3. Numerous red orange and yellow-colored flowers.
4. Good garden performance.

Plants of the new *Alstroemeria* can be compared to plants of the mutation parent, 'Tesronto'. Plants of the new *Alstroemeria* differ from plants of 'Tesronto' in the following characteristics:

1. Plants of the new *Alstroemeria* and 'Tesronto' differ in leaf color.
2. Plants of the new *Alstroemeria* have smaller flowers than plants of 'Tesronto'.
3. Plants of the new *Alstroemeria* and 'Tesronto' differ in flower color.

Plants of the new *Alstroemeria* can be compared to plants of the *Alstroemeria hybrida* 'Tesvoya', not patented. In side-by-side comparisons, plants of the new *Alstroemeria* differ primarily from plants of 'Tesvoya' in the following characteristics:

1. Plants of the new *Alstroemeria* are shorter than plants of 'Tesvoya'.
2. Plants of the new *Alstroemeria* have smaller leaves than plants of 'Tesvoya'.
3. Plants of the new *Alstroemeria* have smaller flowers than plants of 'Tesvoya'.

BRIEF DESCRIPTION OF THE PHOTOGRAPH

The accompanying colored photograph illustrates the overall appearance of the new *Alstroemeria* plant showing the colors as true as it is reasonably possible to obtain in colored reproductions of this type. Colors in the photograph may differ slightly from the color values cited in the detailed botanical description which accurately describe the colors of the new *Alstroemeria* plant.

The photograph comprises a side perspective view of typical flowering plants of 'Teshunte' grown in a ground bed in an outdoor nursery during the summer in De Kwakel, The Netherlands. During the production of the plants, day temperatures ranged from 18° C. to 25° C. and night temperatures ranged from 17° C. to 19° C. Plants were 20 weeks old when the photograph was taken.

DETAILED BOTANICAL DESCRIPTION

Plants used for the following observations and measurements describe plants of the new *Alstroemeria* grown during the autumn in 25-cm containers in a glass-covered greenhouse in De Kwakel, The Netherlands. During the production of the plants, day temperatures ranged from 16° C. to 22° C. and night temperatures ranged from 15° C. to 17° C. Plants were 20 weeks old when the description was taken. Color references are made to The Royal Horticultural Society Colour Chart, 2007 Edition, except where general terms of ordinary dictionary significance are used.

Botanical classification: *Alstroemeria hybrida* 'Teshunte'.

Parentage: Naturally-occurring branch mutation of *Alstroemeria hybrida* 'Tesronto', not patented.

Propagation:

*Type*.—By root divisions.

*Time to produce a rooted young plant, summer*.—About seven weeks at temperatures about 20° C.

*Time to produce a rooted young plant, winter*.—About eight weeks at temperatures about 16° C.

*Root description*.—Fibrous and fleshy; thick to thin; white in color.

*Rooting habit*.—Freely branching; medium density.

*Rhizome length*.—About 3 cm.

*Rhizome diameter*.—About 5 mm.

*Rhizome texture*.—Smooth.

*Rhizome color*.—Close to 195B.

Plant description:

*Plant and growth habit*.—Herbaceous perennial; broadly upright plant habit with medium to long flowering stems, inverted triangle; freely branching habit with about 25 primary lateral branches developing per plant; sturdy and strong plants; moderately vigorous growth habit.

*Plant height*.—About 83.6 cm.

*Plant diameter* (*area of spread*).—About 79.1 cm.

Lateral branch description:

*Aspect*.—Mostly upright to somewhat outwardly spreading.

*Length*.—About 53.7 cm.

*Diameter*.—About 5.5 mm.

*Internode length*.—About 2 cm.

*Strength*.—Moderately strong.

*Texture*.—Smooth, glabrous; waxy.

*Color*.—Close to 200C finely dotted with close to 144A to 144C.

Leaf description:

*Arrangement*.—Alternate; below the peduncles in a single whorl; simple.

*Length*.—About 8 cm.

*Width*.—About 2.7 cm.

*Shape*.—Ovate to elliptic; twisting.

*Apex*.—Acute.

*Base*.—Cuneate.

*Margin*.—Entire.

*Texture, upper and lower surfaces*.—Smooth, glabrous.

*Venation pattern*.—Parallel.

*Color*.—Developing leaves, upper surface: Surface faces downwards; close to 137B strongly tinged with close to 200C; margins, close to 144A to 144B. Developing leaves, lower surface: Surface faces upwards; close to 137B strongly tinged with close to 200C; margins, between 143B and 144A. Fully expanded leaves, upper surface: Surface faces downwards; close to N137C; margins, between 143A and 144A; venation, close to 146A. Fully expanded leaves, lower surface: Surface faces upwards; close to N137C; margins, between 143A and 144A; venation, close to 147A to 147B.

*Petioles*.—Length: About 3.1 cm. Diameter: About 1 mm by 6 mm. Texture, upper and lower surfaces: Smooth, glabrous. Color: Close to 147B.

Flower description:

*Flower type and habit*.—Single zygomorphic flowers arranged in terminal umbels; flowers face mostly outwardly to slightly upright; perianth segments separate; freely flowering habit with about 13 flowers developing per inflorescence and about 325 flowers developing per plant.

*Natural flowering season*.—Plants begin flowering about eight weeks after planting; flowering continuous from summer into the autumn in The Netherlands.

*Fragrance*.—None detected.

*Flower longevity on the plant*.—About ten days; flowers not persistent.

*Flower buds*.—Length: About 2.8 cm. Diameter: About 1 cm. Shape: Narrowly obovate. Color: Close to 145C; towards the apex, close to 174A; venation, close to N137A.

*Umbel height*.—About 10.8 cm.

*Umbel diameter*.—About 14.6 cm.

*Flower diameter* (*horizontal*).—About 4.4 cm.

*Flower length* (*vertical*).—About 5.4 cm.

*Flower depth* (*height*).—About 4.9 cm.

*Perianth*.—Arrangement: Six arranged in two whorls, each whorl with two lateral and one median segments. Size, inner perianth: Length, lateral segments: About 4.7 cm. Width, lateral segments: About 1.7 cm. Length, median segment: About 4.3 cm. Width, median segment: About 1.6 cm. Size, outer perianth: Length, lateral segments: About 4.8 cm. Width, lateral segments: About 2.5 cm. Length, median segment: About 4.6 cm. Width, median segment: About 2.4 cm. Shape, inner perianth, lateral and median segments: Oblanceolate. Shape, outer perianth, lateral and median segments: Obovate. Apex, inner perianth, lateral and median segments: Abruptly acute. Apex, outer perianth, lateral and median segments: Emarginate. Base, inner perianth, lateral and median segments: Narrowly cuneate. Base, outer perianth, lateral and median segments: Long cuneate. Margin, inner perianth, lateral and median segments: Entire. Margin, outer perianth, lateral and median segments: Towards the apex, finely serrate; towards the base, entire. Texture, inner and outer perianths, lateral and median segments: Smooth, glabrous; slightly velvety. Color, inner perianth: When opening, lateral segments, upper surface: Close to 3B; towards the apex, close to 4C; spots, close to 200A to 200B. When opening, median segment, upper surface: Between 3D and 4C; spots, close to 178A. When opening, lateral segments, lower surface: Close to 4A; towards the apex and margins, close to 5D; small apical spot, close to 32D; spots, close to 200C to 200D. When opening, median segment, lower surface: Close to 5D; spots, close to 200C to 200D. Fully opened, lateral segments, upper surface: Close to 9A; towards the apex, close to 9C; spots, close to 203A to 203B; color does not fade with development. Fully opened, median segment, upper surface: Close to 10A, towards the apex, close to 11D; spots, close to 178A; color does not fade with development. Fully opened, lateral segments, lower surface: Close to 8C; towards the apex, close to 11D; apical spot, close to 32C to 32D; spots, close to 200C to 200D. Fully opened, median segment, lower surface: Close to 5D; spots, close to 200C to 200D. Color, outer perianth: When opening, lateral and median segments, upper surface: Close to 11A; towards the base, close to 198C; towards the apex, close to 198A to 198B; central spot, close to N34D. When opening, lateral and median segments, lower surface: Between 10C and 11D; towards the apex, close to 197A; central spot, close to 35A to 35B; venation, close to 144A to 144B. Fully opened, lateral segments, upper surface: Close to 13B to 13C; towards the apex, close to 194B to 194C; base, tinged with close to 31D; margins, striped with close to N34D; central spot, close to N34D; color does not fade with development. Fully opened, median segments, upper surface: Close to 13A; towards the apex, close to 195A; base, tinged with close to 31D; margins, striped with close to N34D; central band, close to 195B; central spot, close to N34D; color does not fade with development. Fully opened, lateral and median segments, lower surface: Close to 16C to 16D; towards the apex, close to 202A; base, close to 35B; margins, close to 35B; central spot, between 171A and 172A; venation, close to 14A.

*Pedicels*.—Length: About 2.3 cm. Diameter: About 2.5 mm. Strength: Moderately strong. Angle: About 15° from vertical. Texture: Smooth, glabrous. Color, upper surface: Close to 186C. Color, lower surface: Close to 146B.

*Reproductive organs*.—Stamens: Quantity per flower: Six. Filament length: About 3.8 cm. Filament color: Close to 179B to 179D; towards the base, close to 150D. Anther shape: Three are oblong and the other three are doubly reniform. Anther length, oblong anthers: About 8 mm. Anther length, reniform anthers: About 3 mm. Anther color: Close to 152B to 152C. Pollen amount: Moderate. Pollen color: Close to 153D. Pistils: Quantity per flower: One. Pistil length: About 3.9 cm. Style length: About 3.9 cm. Style color: Close to 179B; towards the base, lighter than 179B. Stigma shape: Tri-parted; parts, club-shaped, curved. Stigma color: Close to 47C. Ovary color: Close to 143C tinged with between 197A and N200B.

*Fruits and seeds*.—Fruit and seed development have not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate high temperatures of about 35° C. and to be hardy to USDA Hardiness Zone 8.

It is claimed:

1. A new and distinct *Alstroemeria* plant named 'Teshunte' as illustrated and described.

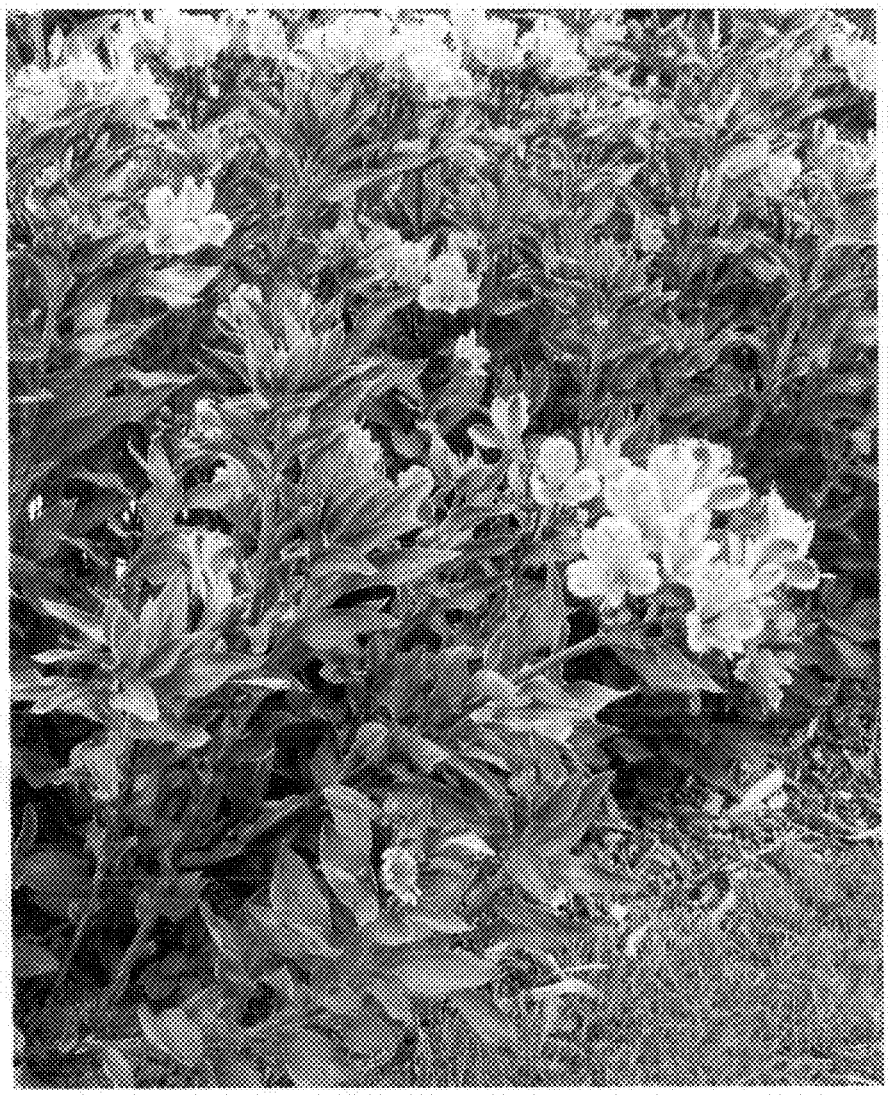

* * * * *